(12) United States Patent
Bertram et al.

(10) Patent No.: US 7,635,398 B2
(45) Date of Patent: Dec. 22, 2009

(54) PURIFICATION OF BIODIESEL WITH ADSORBENT MATERIALS

(75) Inventors: Bryan Bertram, Floyds Knobs, IN (US); Christopher Abrams, Louisville, KY (US); Brian S. Cooke, Clarksville, IN (US)

(73) Assignee: The Dallas Group of America, Inc., Whitehouse, NJ (US)

( * ) Notice: Subject to any disclaimer, the term of this patent is extended or adjusted under 35 U.S.C. 154(b) by 685 days.

(21) Appl. No.: 10/956,856

(22) Filed: Oct. 1, 2004

(65) Prior Publication Data

US 2005/0081436 A1 Apr. 21, 2005

Related U.S. Application Data

(60) Provisional application No. 60/509,959, filed on Oct. 8, 2003.

(51) Int. Cl.
*C10L 8/00* (2006.01)
*C11B 3/10* (2006.01)

(52) U.S. Cl. .............................. 44/605; 44/307; 44/308; 44/320; 554/191; 554/192

(58) Field of Classification Search ................. 554/191, 554/192; 44/605, 320
See application file for complete search history.

(56) References Cited

U.S. PATENT DOCUMENTS

| 4,681,768 | A |   | 7/1987  | Mulflur et al. ............. 426/417 |
|-----------|---|---|---------|--------------------------------------|
| 5,006,356 | A |   | 4/1991  | Munson .................... 426/330.4 |
| 5,252,762 | A | * | 10/1993 | Denton ....................... 554/196 |
| 5,298,639 | A | * | 3/1994  | Toeneboehn et al. ........ 554/192   |
| 5,342,508 | A | * | 8/1994  | Transfeld .................... 208/299 |
| 5,525,126 | A |   | 6/1996  | Basu et al.                          |
| 5,597,600 | A |   | 1/1997  | Munson et al. .......... 426/330.6   |
| 5,917,069 | A | * | 6/1999  | Buckl et al. ................. 554/193 |
| 6,187,355 | B1| * | 2/2001  | Akoh et al. ............... 426/330.3 |
| 6,274,111 | B1| * | 8/2001  | Bauer et al. ................. 423/331 |
| 6,368,648 | B1| * | 4/2002  | Bertram et al. ............. 426/417  |
| 6,638,551 | B1| * | 10/2003 | Levy et al. ............... 426/330.6 |
| 6,642,399 | B2|   | 11/2003 | Boocock                              |
| 6,818,027 | B2| * | 11/2004 | Murcia ......................... 44/550 |
| 7,241,321 | B2| * | 7/2007  | Murcia ......................... 44/589 |
| 7,247,699 | B2| * | 7/2007  | Takabatake et al. ......... 528/480  |
| 7,279,147 | B2| * | 10/2007 | Turkay et al. ................ 423/331 |
| 2003/0181532 | A1 |  | 9/2003 | Parris et al.                        |

FOREIGN PATENT DOCUMENTS

| AT | 387399 B    | 1/1989  |
| DE | 4301686 C1  | 3/1994  |
| EP | 1120379 A1  | 8/2001  |
| WO | WO 93/23142 | 11/1993 |
| WO | WO03/022961 | 3/2003  |

OTHER PUBLICATIONS

Keshavamurthy, et al., Conference Record of the 1994 IEEE International Symposium on Electrical Insulation, pp. 418-421 (Jun. 5-8, 1994).
Yücel, et al., *JAOCS*, vol. 80, No. 4, pp. 373-376 (Apr. 2003).
Ebay.com "Magnidon not Magna Dry Wash Biodiesel No water needed", Jul. 18, 2006.
Florisil®, Synthetic Magnesium Silicate (1997-2005).

* cited by examiner

*Primary Examiner*—Ellen M McAvoy
(74) *Attorney, Agent, or Firm*—Elliot M. Olstein; Raymond J. Lillie

(57) ABSTRACT

A method of purifying a biodiesel fuel by contacting the biodiesel fuel with at least one adsorbent material, such as magnesium silicate. Such method removes impurities, such as soap, formed during the production of biodiesel fuels.

48 Claims, No Drawings

PURIFICATION OF BIODIESEL WITH ADSORBENT MATERIALS

This application is a continuation-in-part of, and claims priority based on provisional application Ser. No. 60/509,959, filed Oct. 8, 2003, the contents of which are incorporated herein by reference in their entirety.

This invention relates to the purification of biodiesel fuel. More particularly, this invention relates to the purification of biodiesel fuel by contacting the biodiesel fuel with at least one adsorbent material, such as magnesium silicate.

Biodiesel is an alternative diesel fuel source to standard petrochemical diesel fuel. Biodiesel may be employed as an alternative fuel for the same types of engines fueled by petrochemical diesel fuel, such as engines for motorized vehicles, such as automobiles, trucks, buses, boats, airplanes, helicopters, snowmobiles, tractors, plows, and other farm vehicles, as well as locomotives, as well as smaller engines, such as those in lawn mowers and snowblowers. Biodiesel also may be employed in power generators and in heating systems in homes and other buildings. Furthermore, biodiesel may be used in combination with petrochemical diesel fuel.

Biodiesel is derived from triacylglycerides (also called triglycerides), which may be obtained from both plant sources, and animal fat sources, such as, for example, soybean oil, rapeseed oil, palm oil, coconut oil, corn oil, cottonseed oil, mustard oil, used cooking oils, float grease from wastewater treatment plants, animal fats such as beef tallow and pork lard, soapstock, crude oils, "yellow grease," i.e., animal or vegetable oils and fats that have been used or generated as a result of the preparation of food by a restaurant or other food establishment that prepares or cooks food for human consumption with a free fatty acid content of less than 15%, and white grease, i.e., rendered fat derived primarily from pork, and/or other animal fats, which has a maximum free fatty acid content of 4%.

The production of biodiesel fuel involves reacting triglycerides with an alcohol (such as methanol, or ethanol, or propanol, for example) in the presence of an alkaline catalyst (such as sodium hydroxide or potassium hydroxide, for example), to produce biodiesel, or monoalkyl fatty acid esters. Glycerol is a by-product of the reaction. When the alcohol employed in the reaction is methanol, the biodiesel fuel is a fatty acid methyl ester (FAME). Methyl esters also may be produced via an enzymatic transesterification of triglycerides, with resultant contaminants to be removed.

The alkaline catalyst is present to speed the reaction; however, a soap is formed during the reaction, e.g., a sodium soap is formed when a sodium hydroxide catalyst is employed. The soap must be removed from the biodiesel fuel because the fuel would leave a residual ash if any soap were present. It is normal practice to employ a "water wash" to remove the soap, similar to that employed in edible oil refining. For example, water is sprayed at low velocity on top of the biodiesel. The excess alcohol and catalyst, as well as soaps, become soluble in the water phase. The soap can cause emulsification of the water and methyl ester, which is a common processing problem. The water and any impurities contained therein are separated from the biodiesel either by gravimetric or mechanical means. The biodiesel then is dried to remove any water remaining in the biodiesel subsequent to the initial separation of water therefrom.

When a large amount of soap is present, the water-washing causes emulsion problems, whereby the fatty acid esters, such as fatty acid methyl esters, will not separate from the water. In addition, water-washing does not eliminate effectively some of the other contaminants, such as sulfur, phosphorus, and any remaining free fatty acids. Methyl esters also may be produced via an enzymatic transesterification of triglycerides with resultant contaminants to be removed.

It is an object of the present invention to purify biodiesel to provide a biodiesel product with improved stability, acceptable for use as a fuel, without the need to use water, and thus avoid the problems resulting therefrom. Another object is to improve the quality of biodiesel produced via the water wash process.

In accordance with an aspect of the present invention, there is provided a method of purifying a biodiesel fuel comprising contacting the biodiesel fuel with at least one adsorbent material.

Adsorbent materials which may be employed in the present invention include, but are not limited to, magnesium silicate, magnesium aluminum silicate, calcium silicate, sodium silicates, activated carbon, silica gel, magnesium phosphate, metal hydroxides, metal oxides, metal carbonates, metal bicarbonates, sodium sesquicarbonate, metal silicates, bleaching clays, bleaching earths, bentonite clay, and alumina. Each of the above-mentioned materials may be employed alone or in combination. When the materials are employed in combination, they may be pre-blended before contacting the biodiesel fuel, or they may brought into contact with the biodiesel fuel separately.

In one embodiment, the at least one adsorbent material comprises magnesium silicate. In one embodiment the magnesium silicate has the following properties:

| | |
|---|---|
| Loss on Ignition | 15% max (dry basis) |
| % MgO | 15% min. (ignited basis) |
| % $SiO_2$ | 67% min. (ignited basis) |
| Soluble salts | 3% max. |
| Mole ratio MgO:$SiO_2$ | 1:1.36 to 1:3.82 |

In another embodiment, the magnesium silicate is an amorphous, hydrated, precipitated, synthetic magnesium silicate having a surface area of at least 300 square meters per gram, and preferably has a surface area from about 400 square meters per gram to about 700 square meters per gram, and more preferably has a surface area from about 400 square meters per gram to about 600 square meters per gram. In addition, such magnesium silicate is preferably employed as coarse particles, with at least 75%, and preferably at least 85% of the particles having a particle size which is greater than 400 mesh, and with no more than 15%, and preferably no more than 5%, all by weight, having a particle size greater than 40 mesh. In most cases, the average particle size of the magnesium silicate employed in accordance with the present invention is in the order of but not limited to 20-175 microns. It is to be understood, however, that the magnesium silicate may have a particle size different than the preferred size.

In addition, the amorphous, hydrated, precipitated magnesium silicate which is employed in accordance with a preferred embodiment of the present invention generally has a bulk density in the order of from 15-35 lbs./cu. ft., a pH of 3-10.8 (5% water suspension) and a mole ratio of MgO to $SiO_2$ of 1:1.0 to 1:4.0.

The following is a specification and typical value for a magnesium silicate which is employed in accordance with an embodiment of the present invention:

TABLE

| Parameter | Specification | Typical Value |
|---|---|---|
| Loss on Ignition at 900° C. | 15% max. | 12% |
| Mole Ratio MgO:SiO$_2$ | 1:2.25 to 1:2.75 | 1:2.60 |
| pH of 5% Water Suspension | 9.5 ± 0.5 | 9.8 |
| Soluble Salts % by wt. | 3.0 max. | 1.0% |
| Average Size, Microns |  | 55 |
| Surface Area (B.E.T.) | 300 M$^2$/g (min.) | 400 |
| Refractive Index |  | Approx. 1.5 |

A representative example of such an amorphous, hydrated, precipitated synthetic magnesium silicate having a surface area of at least 300 square meters per gram is available as Magnesol® Polysorb 30/40, a product of the Dallas Group of America, Inc., Whitehouse, N.J., and also is described in U.S. Pat. No. 4,681,768.

In another embodiment, the magnesium silicate is a magnesium silicate which has a surface area of no more than 150 square meters per gram, preferably from about 50 square meters per gram to about 150 square meters per gram. Preferably, such a magnesium silicate has a mole ratio of MgO to SiO$_2$ of from about 1:3.0 to about 1:3.8, and a pH (5% water suspension) of from about 9.5 to about 10.5. An example of such a magnesium silicate is available as Magnesol® HMR-LS, a product of the Dallas Group of America, Inc., Whitehouse, N.J.

In another embodiment, the magnesium silicate is an amorphous, hydrous, precipitated synthetic magnesium silicate, which has a pH less than about 9.0. As used herein, the term "precipitated" means that the amorphous hydrated precipitated synthetic magnesium silicate is produced as a result of precipitation formed upon the contact of a magnesium salt and a source of silicate in an aqueous medium.

For purposes of the present invention, the pH of the magnesium silicate is the pH of the magnesium silicate as measured in a 5% slurry of the magnesium silicate in water. The pH of the magnesium silicate in a 5% slurry preferably is from about 8.2 to about 8.9, and more preferably from about 8.5 to about 8.8, and most preferably is about 8.5. Examples of such amorphous hydrous precipitated synthetic magnesium silicates are described in U.S. Pat. No. 5,006,356, and also are available as Magnesol® R30 and Magnesol® R60, products of the Dallas Group of America, Inc., Whitehouse, N.J. Magnesol® R30 has an average particle size of 30 microns, and Magnesol® R60 has an average particle size of 60 microns.

In a further embodiment, the magnesium silicate has a pH (5% water suspension) of from about 9.0 to about 9.5.

In another embodiment, the magnesium silicate may be in the form of talc.

It is to be understood, however, that the scope of the present invention is not to be limited to any specific type of magnesium silicate or method for the production thereof.

In general, the biodiesel fuel is contacted with the at least one adsorbent material, such as magnesium silicate as hereinabove described, in an amount effective to remove impurities from the biodiesel fuel. For example, the biodiesel fuel may be contacted with the at least one adsorbent material in an amount of from about 0.01 wt. % to about 20.0 wt. %, based on the weight of the biodiesel fuel, preferably from about 0.5 wt. % to about 4.0 wt. %.

The biodiesel fuel may be derived from any source of triglycerides, including, but not limited to, plant sources, and animal fat or oil sources, including, but not limited to, crude soy, crude oils, used oils, yellow grease, float grease, white grease, soap stock, and any other source of fatty acids.

As stated hereinabove, triacylglycerides are reacted with an alcohol, such as, for example, methanol, ethanol, or propanol, in the presence of a catalyst to produce a mixture of Fatty Acid Methyl Ester (FAME), Fatty Acid Ethyl Ester, and Fatty Acid Propyl Ester, respectively, and by-products described herein. The fatty acid esters are separated from the mixture and heat stripped to remove the residual alcohol.

The fatty acid ester(s) is (are) contacted with the at least one adsorbent material in an amount, such as hereinabove described, effective to remove impurities therefrom. Impurities which may be removed include, but are not limited to, soap, colors, odors, unreacted catalyst, metals and metallic compounds, sulfur, phosphorus, calcium, iron, monoglycerides, diglycerides, polymeric triglycerides, acidic compounds, free and total glycerin, methanol, chlorophyll, water, and sediment, as listed in the specifications for ASTM 6751 for biodiesel, and the European Standard EN14214. The purified biodiesel also will have improved oxidative stability.

The specifications from ASTM 6751 are as follows:

| | |
|---|---|
| Free Glycerin % | 0.020 maximum |
| Total Glycerin, % | 0.240 maximum |
| Flash Point, ° C. | 130° C. maximum |
| Water and Sediment, Vol. % | 0.050 maximum |
| Carbon Residue, % | 0.050 maximum |
| Sulfated Ash, mass % | 0.020 maximum |
| Kinematic Viscosity, cSt at 40° C. | 1.9-6.0 |
| Total Sulfur, mass % | 0.05 maximum |
| Cetane Number | 47 minimum |
| Copper Corrosion | No. 3 maximum |
| Acid Number, mg KOH/gram | 0.80 maximum |
| Phosphorus, Mass % | 0.001 maximum |

The specifications from EN 14214 are as follows:

| Property | Unit | Limits Minimum | Limits Maximum | Test method |
|---|---|---|---|---|
| Ester content | % (m/m) | 96.5 | | EN 14103 |
| Density at 15° C. | kg/m$^3$ | 860 | 900 | EN ISO 3675 |
| | | | | EN ISO 12185 |
| Viscosity at 40° C. | mm$^2$/s | 3.50 | 5.00 | EN ISO 3104 |
| Flash Point | ° C. | 120 | — | prEN ISO 3679 |
| Sulfur content | mg/kg | — | 10.0 | prEN ISO 20846 |
| | | | | prEN ISO 20884 |
| Carbon residue (on 10% distillation residue) | % (m/m) | — | 0.30 | EN ISO 10370 |
| Cetane number | | 51.0 | | EN ISO 5165 |

-continued

| Property | Unit | Limits Minimum | Limits Maximum | Test method |
|---|---|---|---|---|
| Sulfated ash content | % (m/m) | — | 0.02 | ISO 3987 |
| Water content | mg/kg | — | 500 | EN ISO 12937 |
| Total contamination | mg/kg | — | 24 | EN 12662 |
| Copper strip corrosion (3 h at 50° C.) | rating | class 1 | | EN ISO 2160 |
| Oxidation stability, 110° C. | hours | 6.0 | — | EN 14112 |
| Acid value | mg KOH/g | | 0.50 | EN 14104 |
| Iodine value | gr iodine/100 gr | | 120 | EN 14111 |
| Linolenic acid methyl ester | % (m/m) | | 12.0 | EN 14103 |
| Polyunsaturated (>=4 double bonds) methyl esters | % (m/m) | | 1 | |
| Methanol content | % (m/m) | | 0.20 | EN 14110 |
| Monoglyceride content | % (m/m) | | 0.80 | EN 14105 |
| Diglyceride content | % (m/m) | | 0.20 | EN 14105 |
| Triglyceride content | % (m/m) | | 0.20 | EN 14105 |
| Free glycerol | % (m/m) | | 0.02 | EN 14105 |
| | | | | EN 14106 |
| Total glycerol | % (m/m) | | 0.25 | EN 14105 |
| Group I metals (Na + K) | mg/kg | | 5.0 | EN 14108 |
| | | | | EN 14109 |
| Group II metals (Ca + Mg) | mg/kg | | 5.0 | prEN 14538 |
| Phosphorus content | mg/kg | | 10.0 | EN 14107 |

Source: European Standard EN 14214: Automotive fuels-Fatty acid methyl esters (FAME) for diesel engines-Requirements and test methods (approved on 14 Feb. 2003)

The invention now will be described with respect to the examples; however, the scope of the present invention is not intended to be limited thereby.

EXAMPLE 1

Biodiesel fuel samples of 3,733 g (4,440 ml) each, including 20 wt. % fatty acid methyl esters derived from corn oil and 80 wt. % fatty acid methyl esters derived from crude soy oil, were treated with either (i) 1 wt. % Magnesol® R60, or (ii) 2 wt. % Magnesol® R60 at 200° F. for 20 minutes. Unwashed and treated samples were tested for the presence of various impurities, as well as for flash point, kinematic viscosity, cetane number, cloud point, and copper corrosion. The results are given in Table 1 below.

EXAMPLE 2

Biodiesel fuel samples of 100 grams each, including 20 wt. % fatty acid methyl esters derived from corn oil and 80 wt. % fatty acid methyl esters derived from crude soy oil, were treated with either (i) 1 wt % Magnesol®R30 or (ii) from 1 wt. % up to 1.8 wt. % Magnesol® R60 at 200° F. for 20 minutes. Unwashed and treated samples were tested for the presence of free glycerin and total glycerin according to ASTM method D6584. The results are given in Table 2 below.

TABLE 1

| ASTM Spec. | ASTM method of Analysis | Unwashed Methyl Ester | 1% R60 | 2% R60 |
|---|---|---|---|---|
| Free Glycerin, % | D6584 | 0.170 | 0.039 | 0.003 |
| Total Glycerin, % | D6584 | 0.321 | 0.197 | 0.148 |
| Flash Point, ° C. | D93 | NA | 92 | 141 |
| Water and Sediment, vol % | D2709 | 0.60 | 0.005 | 0 |
| Carbon Residue, % | D524 | 0.020 | <0.010 | <0.010 |
| Sulfated Ash, mass % | D874 | 0.025 | 0.000 | 0.00 |
| Kinematic Viscosity, cSt@40° C. | D445 | 3.904 | 4.22 | 4.156 |
| Total Sulfur, Mass % | D5453 | 0.00016 | 0.00025 | 0.00008 |
| Cetane Number | D613 | 51.8 | 53.2 | 55.0 |
| Cloud Point, ° C. | D2500 | −1.0 | −3.0 | 0.0 |
| Copper Corrosion | D130 | 1A | 1A | 1A |
| Acid Number, mg KOH/gram | D664 | 0.23 | 0.48 | 0.40 |
| Phosphorus, Mass % | D4951 | 0.0005 | 0.0002 | 0.0000 |
| ppm Soap | NA | 2411 | 27 | 0 |

TABLE 2

| Sample Description | Free Glycerin % | Total Glycerin % |
|---|---|---|
| Unwashed Methyl Ester | 0.170 | 0.321 |
| 1% Magnesol R30 | 0.029 | 0.156 |
| 1% R60 | 0.037 | 0.185 |
| 1.1% R60 | 0.027 | 0.173 |
| 1.2% R60 | 0.016 | 0.136 |
| 1.4% R60 | 0.008 | 0.133 |
| 1.8% R60 | 0.003 | 0.122 |

EXAMPLE 3

Biodiesel fuel samples of 150 grams each, including fatty acid methyl ester derived from corn oil, were treated with either (i) 1 wt. % Magnesol® R60 or (ii) 2 wt. % Magnesol® R60 at 200° F. for 20 minutes. Unwashed and treated samples were tested for the presence of soap (AOCS method Cc17-79), and free glycerin and total glycerin according to ASTM method D6584. The results are given in Table 3 below.

TABLE 3

| SAMPLE | ppm Soap | Free Glycerin | Total Glycerin |
|---|---|---|---|
| unwashed M.E. | 3382 | 0.339 | 0.531 |
| 1% R60 | 244 | 0.058 | 0.268 |
| 2% R60 | 10 | 0.024 | 0.227 |

EXAMPLE 4

Biodiesel fuel samples of 100 grams each, including fatty acid methyl ester derived from crude soy oil, were treated by either (i) washing with water, followed by drying, or by contacting the samples with (ii) 1 wt. Magnesol®R30; (iii) 2 wt. % Magnesol®R30 or (iv) 4 wt. % Magnesol®R30 at 160° F. for 20 minutes. Unwashed, washed and dried, and Magnesol® treated samples were tested for the presence of soap, and free glycerin and mass percent glycerin according to ASTM method D6584, volume percent water and sediment according to ASTM method D2709, and mass percent sulfated ash according to ASTM method D874. The results are given in Table 4 below.

TABLE 4

| Sample | ppm soap | % Free Glycerin | mass % Glycerin | % water and sediment | Sulfated Ash |
|---|---|---|---|---|---|
| unwashed M.E. | 1722 | 0.292 | 0.402 | 0.2 | 0.033 |
| washed and dried M.E. | 11 | 0 | 0.147 | 0.1 | 0 |
| 1% Treatment Magnesol R30 | 48 | | | | |
| 2% Treatment Magnesol R30 | 0 | 0.031 | 0.145 | 0.06 | 0.001 |
| 4% Treatment Magnesol R30 | 0 | | | | |

EXAMPLE 5

Biodiesel fuel samples of 100 grams each, including fatty acid methyl ester derived from crude soy oil, were treated by contact with either (i) 1 wt. % Magnesol® R60; or (ii) 1 wt. % Magnesol®R30 at 170° F. or 250° F. for 20 minutes. Unwashed and treated samples were tested for the presence of soap, and free and total glycerin according to ASTM method D6584. The results are given in Table 5 below.

| Sample | Treatment temp. | Treatment time. | ppm soap | Free Glycerin | Total Glycerin |
|---|---|---|---|---|---|
| unwashed methyl ester | | | 1900 | 0.086 | 0.204 |
| 1% R60 | 170° F. | 20 minutes | 20 | 0.011 | 0.123 |
| 1% R60 | 250° F. | 20 minutes | 18 | 0.013 | 0.127 |
| 1% Magnesol ®R30 | 170° F. | 20 minutes | 20 | 0.012 | 0.127 |

EXAMPLE 6

Biodiesel fuel samples of 100 grams each, including fatty acid methyl ester derived from yellow grease, were treated either (i) by washing with water, followed by drying; or by contacting the samples with (ii) 1 wt. % Magnesol®R30; (iii) 2 wt. % Magnesol®R30; or (iv) 4 wt. % Magnesol®R30 at 160° F. for 20 minutes. Unwashed, washed and dried, and Magnesol® treated samples were tested for the presence of soap. The results are given in Table 6 below. In this example, there was a significant amount of unreacted methanol boiling off while heating the samples to treatment temperature. This methanol should have been removed during the heat stripping step.

TABLE 6

| Sample | Ppm Soap |
|---|---|
| Unwashed M.E. | 5971 |
| Washed and dried M.E. | 77 |
| 1% treatment Magnesol ®R30 | 3723 |
| 2% treatment Magnesol ®R30 | 2381 |
| 4% treatment Magnesol ®R30 | 1914 |

The excess methanol may have interfered with the ability of the Magnesol®R30 to adsorb soap. Therefore, the experiment was repeated after removing the excess methanol (See Example 7 below).

EXAMPLE 7

Biodiesel fuel samples of 100 grams each, including fatty acid methyl ester derived from yellow grease (used in Example 6), were treated after boiling for 2 hours to remove excess methanol by contacting the samples with (i) 2 wt. % Magnesol®R30; (ii) 4 wt. % Magnesol®R30; or (iii) 8 wt. % Magnesol®R30 at 160° F. for 20 minutes. Unwashed, and Magnesol®R30 treated samples were tested for the presence of soap. The results are given in Table 7 below.

TABLE 7

| Sample | ppm Soap |
|---|---|
| unwashed M.E. | 4986 |
| 2% Treatment Magnesol ®R30 | 1490 |
| 4% Treatment Magnesol ®R30 | 79 |
| 8% Treatment Magnesol ®R30 | 9 |

The results confirmed that the excess methanol interfered with the purification of the biodiesel sample.

EXAMPLE 8

Procedure and Reaction Conditions

I. Biodiesel Production 60 gallons of both crude soybean oil methyl esters and yellow grease methyl esters were produced at the biodiesel pilot plant located at the Biomass Energy Conversion Facility (BECON) in Nevada, Iowa. The biodiesel pilot plant is operated by Iowa State University and was constructed using major biodiesel manufacturing facilities as the model. The procedure for making the soybean and yellow grease methyl esters is described below.

Soybean Feedstock

The reaction process for the soybean oil based methyl ester was completed in three steps. Step One involved adding 80% of the methanol and catalyst and removing the glycerin after reaction completion. During Step Two, the remaining 20% of methanol and catalyst were added and the glycerin was separated after reaction completion. Step Three was the stripping of methanol from the reacted biodiesel.

Step One: Primary Reaction

Crude dried and partially degummed soybean oil containing 0.70% FFA weighing 520 lb. (approximately 69 gallons) was added to the reaction tank. 95.68 lb of methanol and 6.37 lb. of sodium methoxide were added and the materials were mixed and heated until the reaction temperature reached 140° F. after 30 minutes. The reaction was allowed to continue at 140° F. for an additional 1.5 hours (total of 2 hours reaction time) and then the mixing and heating were stopped. After 8 hours of separation time, the glycerin phase was separated from the methyl ester phase. The amount of glycerin removed was 82.7 lb.

Step Two: Secondary Reaction

To the remaining methyl ester/soybean oil an additional 23.92 lb. of methanol and 1.59 lb. of sodium methoxide were added and the reaction conditions in step one were repeated. The amount of glycerin removed was 9.8 lb.

Step Three: Methanol Stripping

The remaining methyl esters were passed through the flash evaporator to remove the excess methanol. The flash tank vacuum was maintained at 25-26 mm Hg and the spray temperature in the flash tank was 240° F. The condenser water flow rate was 3 gpm and the recirculation time was 45 minutes. The final flash point of the methyl esters was 143° F.

The 60 gallons of methyl esters produced from soybean feedstock were placed into a 70-gallon capacity-mixing tank. The methyl esters were recirculated for about 10 minutes to ensure that the mixture was uniform. Approximately 3 gallons of the methyl ester were placed into a 5-gallon container to be tested at a later time.

Yellow Grease Feedstock

The reaction process for the yellow grease based methyl esters was completed in four steps. Step One was the pretreatment to convert the FFA to methyl esters. Step Two involved adding 80% of the methanol and catalyst and removing the glycerin after reaction completion. During Step Three the remaining 20% of methanol and catalyst were added and the glycerin was separated after reaction completion. During Step Four the methanol was stripped from the reacted biodiesel.

Step One: Pretreatment

Yellow grease, weighing 480 lb. (approximately 64 gallons) and containing 11.6% FFA, was added to the reaction tank. Methanol (125.04 lb.) and Sulfuric acid (2.78 lb.) were added to the yellow grease and the materials were mixed and heated until the reaction temperature reached 140° F. after 30 minutes. The reaction continued for an additional 1.5 hours. The mixture was allowed to separate for 8 hours in order to confirm the effective conversion of the FFA to methyl esters. The upper phase contained methanol, sulfuric acid and methyl esters and weighed approximately 147.82 lb. The lower phase, consisting of yellow grease, weighed about 460 lb. and contained 1.67% FFA.

Step Two: Primary Reaction

To the pre-treated grease from Step One, 84.64 lb. of methanol and 8.21 lb. of sodium methoxide were added. The materials were mixed and heated until the reaction reached 140° F. after 30 minutes. The reaction was allowed to continue at 140° F. for an additional 1.5 hours (total of 2 hours reaction time) and then the mixing and heating were stopped. After 8 hours of separation time, the glycerin phase was separated from the methyl ester phase. The amount of glycerin removed was 102 lb. Approximately 10 lb. of the yellow grease/methyl ester was lost.

Step Three: Secondary Reaction

To the remaining 450 lb. methyl ester/yellow grease an additional 21.16 lb. of methanol and 2.05 lb. of sodium methoxide were added and the reaction conditions in step one were repeated. The amount of glycerin removed was 10 lb.

Step Four: Methanol Stripping

The remaining methyl esters were passed through the flash evaporator to remove the excess methanol. The flash tank vacuum was maintained at 25-26 mm Hg and the spray temperature in the flash tank was 240° F. The condenser water flow rate was 3 gpm and the recirculation time was 45 minutes.

The 60 gallons of methyl esters produced from yellow grease feedstock was placed into a 70-gallon capacity-mixing tank. The methyl ester was recirculated for about 10 minutes to ensure that the mixture was uniform. Approximately 3 gallons of the methyl ester were placed into a 5-gallon container to be tested at a later time.

II Water Wash Procedure

Soybean Feedstock

Twenty gallons of crude soybean biodielsel were water washed using four successive washes at 140° F. soft water wash tank. Each wash was performed using 50% of the volume of the biodiesel (see Table 8). The first two water washes were performed using no agitation (just spraying water into tank) while the third and forth washes were performed using agitation. The water from each wash was removed by gravity separation and discarded.

The washed biodiesel then was placed through the flash evaporator to remove excess water. The flash tank vacuum was maintained at 27-28 mm Hg and the spray temperature of the tank was 240° F. The condenser flow rate was 1 gpm, the throttling pressure was 25 psig and the recirculation time was 30 minutes. The finished biodiesel was then collected into 5-gallon containers and saved for further analysis.

TABLE 8

Water Washed Soybean Biodiesel

| Sample Description | # Water Washes | Amount Water/Wash | % H$_2$O |
|---|---|---|---|
| Water Washed ME | 4 | 220 lb. | 0.017 |

Yellow Grease Feedstock

Twenty gallons of the yellow grease biodiesel were water washed using a total of five successive washes at 140° F. using soft water in the water wash tank. Each wash was performed using 50% of the volume of the biodiesel (see Table 9). The first three water washes were performed using no agitation while the forth and fifth washes were performed using agitation. The water from each wash was removed by gravity separation and discarded (separation time was 45 minutes/water wash).

TABLE 9

Water Washed Yellow Grease Biodiesel

| Sample Description | # Water Washes | Amount Water/Wash | % H$_2$O |
|---|---|---|---|
| Water Washed ME | 5 | 220 lb. | 0.019 |

The washed biodiesel the was placed through the flash evaporator to remove excess water. The flash tank vacuum was maintained at 27-28 mm Hg and the spray temperature of the tank was 240° F. The condenser flow rate was 1 gpm, the throttling pressure was 25 psig and the recirculation time was 30 minutes. The finished biodiesel was then collected into 5-gallon containers and saved for further analysis.

III. Adsorbent Purification with Synthetic Magnesium Silicate

Soybean Methyl Esters

In order to confirm an appropriate treatment level, a 200 g sample of the biodiesel was treated in the laboratory with 1% by weight (2 g) of MAGNESOL® R60 at 16° F. The material was gravity filtered after 5 minutes contact time was achieved. The acid value and soap content were checked on the sample before and after the treatment (see Table 10 below).

TABLE 10

Initial Soybean Biodiesel Laboratory Testing

| Sample Description | Flash Point (° C.) | Acid Value (mg KOH/g) | Soap Content (ppm) |
|---|---|---|---|
| Initial ME | 143 | 0.61 | 651 |
| After 1% R60 | NT | 0.40 | 9 |

Twenty gallons of methyl esters produced from the soybean feedstock (not water washed) were placed into a 70-gallon capacity-mixing tank. The 20 gallons were circulated through a heat exchanger until the tank temperature was 170° F. (77° C.). MAGNESOL® R60 was added to the methyl esters at the predetermined level of 1% by weight (1.5 lb. MAGNESOL®) and the material was mixed for 10 minutes. The methyl ester/MAGNESOL® mixture was recirculated through a sock filter that contained a 5-micron polypropylene filter sock (approximately 6" diameter by 3' length. The filtrate appeared clear after about 10 minutes of circulation through the filter and a sample was taken and checked for soap (See Table 11). The filtrate was collected into 5-gallon containers and saved for further analysis.

TABLE 11

Treatment of Soybean Biodiesel with MAGNESOL® R60

| Sample Description | Methyl Ester Wt. | MAGNESOL® R60 Wt. | % treatment | Treatment Temperature | Soap Content (ppm) |
|---|---|---|---|---|---|
| Initial ME R60 | 146.6 Lb. | | | | 651 |
| Treated ME | | 1.5 lb. | 1.0 | 170° F. | 8 |

Yellow Grease Methyl Esters

In order to confirm an appropriate treatment level, a 200 g sample of the biodiesel was treated in the laboratory with 2% by weight (4 g) of MAGNESOL® R60 AT 160° F. The soap and flash point were tested before and after the treatment (see Table 12)

TABLE 12

Initial Yellow Grease Biodiesel Laboratory Testing

| Sample Description | Flash Point (° C.) | Soap Content (ppm) |
|---|---|---|
| Initial ME | 140 | 2600 |
| after 2% R60 | 145 | 10 |

15 Gallons of the methyl ester made from yellow grease feedstock (not water washed) were pumped into the mix tank to be treated with MAGNESOL® R60. A one-gallon sample was collected. The remaining 14 gallons were treated with MAGNESOL® at 170° F. for 10 minutes and then the filter was started and recirculated for about 20 minutes (Table 13). The biodiesel was collected into 5-gallon containers for further analysis.

TABLE 13

Treatment of Yellow Grease Biodiesel with MAGNESOL ® R60

| Sample Description | Methyl Ester Wt. | MAGNESOL ® R60 Wt. | % Treatment | Treatment Temperature | Soap Content (ppm) |
|---|---|---|---|---|---|
| Initial ME | 102.6 lb. | | | | 2600 |
| R60 Treated ME | | 2.05 lb. | 2.0 | 170° F. | 22 |

IV Analytical Testing of Biodiesel Samples

The biodiesel samples that were collected were labeled as follows:

S1=unwashed, untreated soybean biodiesel
S2=washed and dried soybean biodiesel
S3=1% MAGNESOL® R60 treated soybean biodiesel
Y1=unwashed, untreated yellow grease biodiesel
Y2=washed and dried yellow grease biodiesel
Y3=2% MAGNESOL® R60 treated yellow grease biodiesel.

ASTM D6751

All samples were sent to a recognized analytical laboratory for the entire ASTM D6751 testing.

Additional Parameters Tested

All samples were tested for additional parameters, including: metal content (P, Na, Mg, Ca), soap, viscosity and oxidative stability.

Data and Results

Soybean Oil Based Biodiesel

TABLE 14

ASTM D6751 Results for Soybean Biodiesel

| ASTM SPECIFICATION | ASTM D6751 specification | Unwashed, Untreated M.E. | 1% MAGNESOL ® R60 | Washed And Dried M.E. |
|---|---|---|---|---|
| Free Glycerin, % | 0.020 maximum | 0.033 | 0.005 | 0.002 |
| Total Glycerin, % | 0.240 maximum | 0.209 | 0.191 | 0.196 |
| Flash Point, ° C. | 130 minimum | >190 | 200 | 163 |
| Water and Sediment, vol. % | 0.050 maximum | 0.10 | 0.04 | 0.00 |
| Carbon Residue, % | 0.050 maximum | <0.010 | <0.010 | 0.050 |
| Sulfated Ash, mass % | 0.020 maximum | 0.000 | 0.000 | 0.005 |
| Kinematic Viscosity, cSt@40° C. | 1.9-6.0 | 4.127 | 4.097 | 4.207 |
| Total Sulfur, mass % | 0.05 maximum | 0.00006 | 0.00002 | 0.00007 |
| Cetane Number | 47 minimum | 51.0 | 51.3 | 55.9 |
| Cloud Point, ° C. | Report | 0.0 | 0.0 | 0.0 |
| Copper Corrosion | No. 3 maximum | 1a | 1a | 1a |
| Acid Number, mg KOH/gram | 0.80 maximum | 0.32 | 0.27 | 0.31 |
| Phosphorus, mass % | 0.001 | 0.0007 | 0.0005 | 0.0006 |

The results from the ASTM D6751 testing for the soybean methyl esters are summarized in Table 14. The untreated, unwashed soybean methyl ester did not meet the ASTM D6751 specifications. The washed and dried methyl ester and the 1% MAGNESOL® treated methyl ester were able to meet all ASTM specifications. The results show that the traditional water washing of the methyl ester could be replaced completely by the adsorptive treatment with MAGNESOL®.

TABLE 15

Additional Parameters Tested for Soybean Biodiesel

| Parameter | Method | Unwashed, Untreated M.E. | 1% MAGNESOL ® R60 | Washed And Dried M.E. |
|---|---|---|---|---|
| Viscosity at 40° C., mm²/sec | ISO 3104 | 4.1 | 4.1 | 4.2 |
| Oxidation stability | EN 14112 | 0.5 | 3.7 | 0.2 |

TABLE 15-continued

Additional Parameters Tested for Soybean Biodiesel

| Parameter | Method | Unwashed, Untreated M.E. | 1% MAGNESOL ® R60 | Washed And Dried M.E. |
|---|---|---|---|---|
| at 110° C., hours | | | | |
| Methanol content, % | EN14110 | 0.113 | 0.011 | <0.001 |
| Metals I Na, mg/kg | AA | 3 | <1 | 5 |
| Metals II Ca, mg/kg | EN 14538 | 0 | 0 | 0 |
| Metals II Mg, mg/kg | EN 14538 | 0 | 0 | 0 |
| Phosphorus content, mg/kg | EN 14107 | <1 | <1 | <1 |
| Soap, mg/kg | AOCS Cc17-79 | 651 | 4 | 13 |

Some additional parameters that were tested on the soybean methyl esters are reported in Table 15. The oxidative stability of biodiesel is a very important parameter that relates to the storage and thermal stability of the biodiesel fuel. The oxidative stability of the biodiesel was improved significantly by treatment with MAGNESOL® when compared to the unwashed, untreated methyl ester and the traditional water wash method (86% and 95% improvement).

There was not any significant amount of metals or soap (4 ppm) after the treatment and filtration of the methyl esters with MAGNESOL®, while the water washed biodiesel contained 5 ppm sodium and 13 ppm soap.

Yellow Grease Based Biodiesel

The results from ASTM D6751 testing for the yellow grease methyl esters are summarized in Table 16. The untreated, unwashed soybean methyl ester and the washed and dried methyl esters did not meet the ASTM D6751 specifications. The washed and dried methyl ester did not meet the specification for free glycerin and water and sediment. There was a very high soap content (see Table 17) in the unwashed, untreated methyl ester, which may have led to poor separation and emulsification, which could explain the inability to meet the ASTM specifications.

The 2% MAGNESOL® treated yellow grease methyl ester was able to meet all ASTM D6751 specifications. The results show that the adsorptive treatment of the yellow grease methyl esters yielded a more pure biodiesel than that obtained by the traditional water washing method.

TABLE 16

ASTM D6751 Results for Yellow Grease Methyl Ester

| ASTM Specification | ASTM D6751 specification | Unwashed, Untreated M.E. | 2% MAGNESOL ® R60 | Washed And Dried M.E. |
|---|---|---|---|---|
| Free Glycerin, % | 0.020 maximum | 0.063 | 0.004 | 0.037 |
| Total Glycerin, % | 0.240 maximum | 0.220 | 0.147 | 0.185 |
| Flash Point, ° C. | 130 minimum | 179 | 168 | >190 |
| Water and Sediment, vol. % | 0.050 maximum | 0.70 | 0.005 | 0.06 |
| Carbon Residue, % | 0.050 maximum | 0.060 | 0.000 | 0.013 |
| Sulfated Ash, mass % | 0.020 maximum | 0.007 | 0.002 | 0.004 |
| Kinematic Viscosity, cSt@40° C. | 1.9-6.0 | 5.095 | 5.060 | 5.107 |
| Total Sulfur, mass % | 0.05 maximum | 0.00146 | 0.00133 | 0.00139 |
| Cetane Number | 47 minimum | 57.8 | 57.4 | 60.3 |
| Cloud Point, ° C. | Report | 10.0 | 9.0 | 9.0 |
| Copper Corrosion | No. 3 maximum | 1a | 1a | 1a |
| Acid Number, mg KOH/gram | 0.80 maximum | 0.21 | 0.32 | 0.27 |
| Phorphorus, mass % | 0.001 maximum | 0.0009 | 0.0008 | 0.0008 |

TABLE 17

Additional Parameters Tested for Yellow Grease Biodiesel

| EN 14214 Specification | EN 14214 Method | Unwashed, Untreated M.E. | 2% MAGNESOL ® R60 | Washed And Dried M.E. |
|---|---|---|---|---|
| Viscosity at 40° C. (mm²/sec) | ISO 3104 | 5.0 | 4.9 | 5.1 |
| Oxidation stability at 110° C., hours | EN 14112 | 0.5 | 4.3 | 0.2 |
| Methanol content, % | EN 14110 | 0.116 | 0.002 | <0.001 |
| Metals I Na, mg/kg | AA | 16 | <1 | 3 |
| Metals II Ca, mg/kg | EN 14538 | 0 | <1 | 0 |
| Metals II Mg, mg/kg | EN 14538 | 0 | 1 | 0 |
| Phosphorus content, mg/kg | EN 14107 | <1 | <1 | 1 |
| Soap, mg/kg | AOCS Cc17 - 79 | 2458 | 4 | 91 |

Some additional parameters that were tested on the yellow grease methyl esters are reported in Table 17. The oxidative stability of the biodiesel was improved significantly by treatment with MAGNESOL® when compared to the unwashed untreated sample (88% improvement). The oxidative stability was also significantly improved when compared to the traditional water wash method (95% improvement).

There was not any significant amount of metals (all <1 ppm) or soap (4 ppm) after the treatment and filtration of the methyl esters with MAGNESOL®, while the water washed biodiesel contained 91 ppm soap.

EXAMPLE 9

A 400 g sample of methyl ester (biodiesel) produced from refined bleached, deodorized (RBD) soybean oil was treated with MAGNESOL® R60, or MAGNESOL® 300R (a blend of 30% sodium silicate and 70% MAGNESOL® R60), or MAGNESOL® 600R (a blend of 60% sodium silicate and 40% MAGNESOL® R60), or MAGNESOL® 900R (a blend of 90% sodium silicate and 10% MAGNESOL® R60) at 180° F. for 20 minutes in the amounts shown in Table 18 below.

TABLE 18

| Adsorbent | Wt. % |
|---|---|
| MAGNESOL R60 | 2.0 |
| MAGNESOL 300R | 1.0 |
| MAGNESOL 300R | 1.25 |
| MAGNESOL 300R | 1.5 |
| MAGNESOL 300R | 1.75 |
| MAGNESOL 300R | 2.0 |
| MAGNESOL 600R | 0.75 |
| MAGNESOL 900R | 0.50 |

The samples then were tested for the presence of free fatty acids (FFA) and soap (ppm). The results are given in Table 19 below.

TABLE 19

| Sample | % FFA | Soap (ppm) |
|---|---|---|
| Blank | 0.88 | 19 |
| 2% MAGNESOL ® R60 | 0.72 | 0 |
| 1.0% MAGNESOL ® 300R | 0.49 | 23 |
| 1.25% MAGNESOL ® 300R | 0.36 | N/A |
| 1.5% MAGNESOL ® 300R | 0.29 | N/A |
| 1.75% MAGNESOL ® 300R | 0.20 | N/A |
| 2.0% MAGNESOL ® 300R | 0.24 | 16 |
| 0.75% MAGNESOL ® 600R | 0.42% | 18 |
| 0.50% MAGNESOL ® 900R | 0.41 | 34 |

EXAMPLE 10

A 400 g sample of crude methyl ester (biodiesel) produced from soybean oil was treated with MAGNESOL® R60 or MAGNESOL® 700R, a blend of 70% sodium silicate and 30% MAGNESOL® R60, in the amounts shown in Table 20 below for 20 minutes at temperatures from 78° F. to 350° F. also as shown in Table 20 below. The treated samples then were tested for the presence of free fatty acids (FFA), soap (ppm), and chlorophyll (ppm). The results are given in Table 20 below.

TABLE 20

| Adsorbent | Wt. % | Temp. | Time | % FFA | Soap (ppm) | % Free Glycerin | % Total Glycerin | Chlorophyll (ppm) |
|---|---|---|---|---|---|---|---|---|
| MAGNESOL ® R60 | 0.50 | 200° F. | 20 min. | 0.46 | 0 | — | — | — |
| MAGNESOL ® R60 | 0.75 | 200° F. | 20 min. | 0.45 | 0 | — | — | — |

TABLE 20-continued

| Adsorbent | Wt. % | Temp. | Time | % FFA | Soap (ppm) | % Free Glycerin | % Total Glycerin | Chlorophyll (ppm) |
|---|---|---|---|---|---|---|---|---|
| MAGNESOL ® 700R | 0.75 | 200° F. | 20 min. | 0.28 | 143 | — | — | — |
| MAGNESOL ® 700R | 0.75 | 150° F. | 20 min. | 0.21 | 56 | — | — | — |
| MAGNESOL ® R60 | 0.75 | 78° F. | 20 min. | 0.49 | 6 | — | — | 2.96 |
| MAGNESOL ® R60 | 0.75 | 150° F. | 20 min. | 0.48 | 0 | — | — | 2.00 |
| MAGNESOL ® R60 | 0.75 | 200° F. | 20 min. | 0.46 | 0 | — | — | 0.91 |
| MAGNESOL ® R60 | 0.75 | 300° F. | 20 min. | 0.46 | 0 | — | — | 1.00 |
| MAGNESOL ® R60 | 0.75 | 350° F. | 20 min. | 0.46 | 0 | — | — | 0.97 |
| Before Treating | — | — | — | 0.87 | 60 | 0.002 | 0.195 | 3.2 |

The disclosure of all patents and publications (including published patent applications) are hereby incorporated by reference to the same extent as if each patent and publication were incorporated individually by reference.

It is to be understood, however, that the scope of the present invention is not to be limited to the specific embodiments described above. The invention may be practiced other than as particularly described and still be within the scope of the accompanying claims.

What is claimed is:

1. A method of purifying a crude biodiesel fuel, comprising:
   contacting said crude biodiesel fuel with at least one adsorbent material, wherein said at least one adsorbent material comprises magnesium silicate, and wherein said biodiesel fuel is a product of reacting triglycerides with an alcohol, thereby providing a purified biodiesel fuel which includes at least one monoalkyl fatty acid ester.

2. The method of claim 1 wherein said magnesium silicate has magnesium silicate has surface area of at least 300 square meters per gram.

3. The method of claim 2 wherein said magnesium silicate has a surface area of at least 400 to about 700 square meters per gram.

4. The method of claim 2 wherein said magnesium silicate has a particle size of from about 20 microns to about 175 microns.

5. The method of claim 2 wherein said magnesium silicate has a bulk density of from about 15 to about 35 pounds per cubic foot.

6. The method of claim 1 wherein said magnesium silicate is an amorphous hydrous precipitated synthetic magnesium silicate, said magnesium silicate having been treated to reduce the pH thereof to less than about 9.0.

7. The method of claim 6 wherein said magnesium silicate has a pH in a 5% slurry of from about 8.2 to about 8.9.

8. The method of claim 7 wherein said magnesium silicate has a pH in a 5% slurry of from about 8.5 to about 8.8.

9. The method of claim 1 wherein said magnesium silicate has a surface area of no more than 150 square meters per gram.

10. The method of claim 9 wherein said magnesium silicate has a surface area of from about 50 square meters per gram to about 150 square meters per gram.

11. The method of claim 10 wherein said magnesium silicate has a mole ratio of MgO to $SiO_2$ of from about 1:3.0 to about 1:3.8 and a pH in a 5% water suspension of from about 9.5 to about 10.5.

12. The method of claim 1 wherein said magnesium silicate has a pH of from about 9.0 to about 9.5.

13. The method of claim 1 wherein said crude biodiesel fuel is contacted with said magnesium silicate in an amount of from about 0.01 wt.% to about 20.0 wt.%, based on the weight of said biodiesel fuel.

14. The method of claim 13 wherein said crude biodiesel fuel is contacted with said magnesium silicate in an amount of from about 0.5 wt.% to about 4.0 wt.%, based on the weight of said biodiesel fuel.

15. The method of claim 1 wherein free fatty acids are removed from said crude biodiesel fuel.

16. The method of claim 1 wherein chlorophyll is removed from said crude biodiesel fuel.

17. The method of claim 1 wherein methanol is removed from said crude biodiesel fuel.

18. The method of claim 17 wherein said methanol is trace methanol.

19. The method of claim 1 wherein glycerin is removed from said crude biodiesel fuel.

20. The method of claim 1 wherein unreacted catalyst is removed from said crude biodiesel fuel.

21. A method for treating a crude biodiesel fuel, said biodiesel fuel including a fatty acid methyl ester, said fatty acid methyl ester having been prepared by reacting methanol with triglycerides in the presence of a catalyst, said method comprising:
   treating said crude biodiesel fuel with magnesium silicate to remove one or more of soap, unreacted catalyst, sulfur, phosphorus, calcium, iron, monoglycerides, diglycerides, polymeric triglycerides, acidic compounds, glycerin, chlorophyll, water, sediment, and remaining methanol.

22. The method of claim 21 wherein said magnesium silicate has a surface area of at least 300 square meters per gram.

23. The method of claim 22 wherein said magnesium silicate has a particle size of from about 20 microns to about 175 microns.

24. The method of claim 21 wherein said magnesium silicate is an amorphous hydrous precipitated synthetic magnesium silicate, said magnesium silicate having been treated to reduce the pH thereof to less than about 9.0.

25. The method of claim 21 wherein said crude biodiesel fuel is contacted with said magnesium silicate in an amount of from about 0.01 wt. % to about 20.0 wt. %, based on the weight of said biodiesel fuel.

26. The method of claim 25 wherein said crude biodiesel fuel is contacted with said magnesium silicate in an amount of from about 0.5 wt. % to about 4.0 wt. %, based on the weight of said biodiesel fuel.

27. A method of purifying a crude biodiesel fuel, wherein said crude biodiesel fuel is produced by reacting triglycerides with an alcohol in the presence of an alkali catalyst, thereby producing a crude biodiesel fuel including at least one monoalkyl fatty acid ester and at least one impurity including soap, said method comprising:
contacting said crude biodiesel fuel with at least one adsorbent material, wherein said at least one adsorbent material comprises magnesium silicate, thereby removing soap from said crude biodiesel fuel.

28. The method of claim 27 wherein said contacting of said crude biodiesel fuel with said at least one adsorbent material further removes at least one of unreacted catalyst, sulfur, phosphorus, calcium, iron, monoglycerides, diglycerides, polymeric triglycerides, acidic compounds, glycerin, chlorophyll, water, sediment, and remaining methanol from said crude biodiesel fuel.

29. The method of claim 28 wherein chlorophyll is removed from said crude biodiesel fuel.

30. The method of claim 28 wherein remaining methanol is removed from said crude biodiesel fuel.

31. The method of claim 28 wherein glycerin is removed from said crude biodiesel fuel.

32. The method of claim 28 wherein unreacted catalyst is removed from said crude biodiesel fuel.

33. A method of purifying a crude biodiesel fuel, said biodiesel fuel including a monoalkyl fatty acid ester, said monoalkyl fatty acid ester having been prepared by reacting triglycerides with an alcohol, said method comprising:
contacting said crude biodiesel fuel with at least one adsorbent material, wherein said at least one adsorbent material comprises magnesium silicate, and wherein during said purifying of said crude biodiesel fuel, said crude biodiesel fuel is not contacted with water.

34. The method of claim 33 wherein one or more of soap, unreacted catalyst, sulfur, phosphorus, calcium, iron, monoglycerides, diglycerides, polymeric triglycerides, acidic compounds, glycerin, chlorophyll, water, sediment, and remaining methanol is removed from said crude biodiesel fuel.

35. The method of claim 34 wherein soap is removed from said crude biodiesel fuel.

36. The method of claim 34 wherein chlorophyll is removed from said crude biodiesel fuel.

37. The method of claim 34 wherein remaining methanol is removed from said crude biodiesel fuel.

38. The method of claim 34 wherein glycerin is removed from said biodiesel fuel.

39. The method of claim 27 wherein said magnesium silicate has a surface area of at least 300 square meters per gram.

40. The method of claim 27, wherein said magnesium silicate has a particle size of from about 20 microns to about 175 microns.

41. The method of claim 27, wherein said magnesium silicate is an amorphous, hydrous, precipitated magnesium silicate, said magnesium silicate having been treated to reduce the pH thereof to less than about 9.0.

42. The method of claim 27, wherein said crude biodiesel fuel is contacted with said magnesium silicate in an amount of from about 0.01 wt.% to about 20.0 wt.%, based on the weight of said biodiesel fuel.

43. The method of claim 42, wherein said crude biodiesel fuel is contacted with said magnesium silicate in an amount of from about 0.5 wt.% to about 4.0 wt.%, based on the weight of said biodiesel fuel.

44. The method of claim 33 wherein said magnesium silicate has a surface area of at least 300 square meters per gram.

45. The method of claim 33, wherein said magnesium silicate has a particle size of from about 20 microns to about 175 microns.

46. The method of claim 33, wherein said magnesium silicate is an amorphous hydrous, precipitated magnesium silicate, said magnesium silicate having been treated to reduce the pH thereof to less than about 9.0.

47. The method of claim 33, wherein said crude biodiesel fuel is contacted with said magnesium silicate in an amount of from about 0.01 wt.% to about 20.0 wt.%, based on the weight of said biodiesel fuel.

48. The method of claim 47, wherein said crude biodiesel fuel is contacted with said magnesium silicate in an amount of from about 0.5 wt.% to about 4.0 wt.%, based on the weight of said biodiesel fuel.

* * * * *